United States Patent [19]

Kennedy et al.

[11] Patent Number: 6,119,266
[45] Date of Patent: Sep. 19, 2000

[54] WELDING HOOD WITH PERISCOPIC VIEW PIECE

[76] Inventors: David E. Kennedy, P.O. Box 336;
Larry Kennedy, Rte. 2, Box 2190,
both of Advance, Mo. 63730

[21] Appl. No.: 09/201,042

[22] Filed: Nov. 30, 1998

[51] Int. Cl.$^7$ ....................................................... A61F 9/06
[52] U.S. Cl. ............................................................. 2/8
[58] Field of Search .................................. 2/8, 424, 9, 10, 2/15; 219/147

[56] References Cited

U.S. PATENT DOCUMENTS 1,885,744  11/1932  Malcom .
2,211,238   8/1940  Links .
3,978,526   9/1976  Mitchell et al. ............................ 2/422
4,646,363   3/1987  Wood .
5,331,473   7/1994  Petersen .
5,398,341   3/1995  Trapple .

Primary Examiner—Michael A. Neas
Attorney, Agent, or Firm—Hovey, Williams, Timmons & Collins

[57] ABSTRACT

A welding hood is provided with a periscopic view piece to provide an elevated effective line of sight for viewing over and around objects during welding operations. The welding hood includes a face mask and a head band or other support which supports and positions the mask on the welder's head. A view piece includes an objective window which is normally tinted or filtered to protect the welder's eyes from brilliant light, a first mirror behind the objective window, and a second, lower mirror oriented to reflect the image passing through the objective window and reflected by the first mirror to the second mirror along the welder's unaided line of sight. The first mirror may be tiltably mounted to increase the field of view, and the objective window and the first mirror may be mounted on a housing coupled to the remainder of the mask by an extensible member such as a bellows to permit the welder to adjust the displacement between the first mirror and the second mirror and thus the displacement between the effective line of sight and his unaided line of sight.

17 Claims, 2 Drawing Sheets

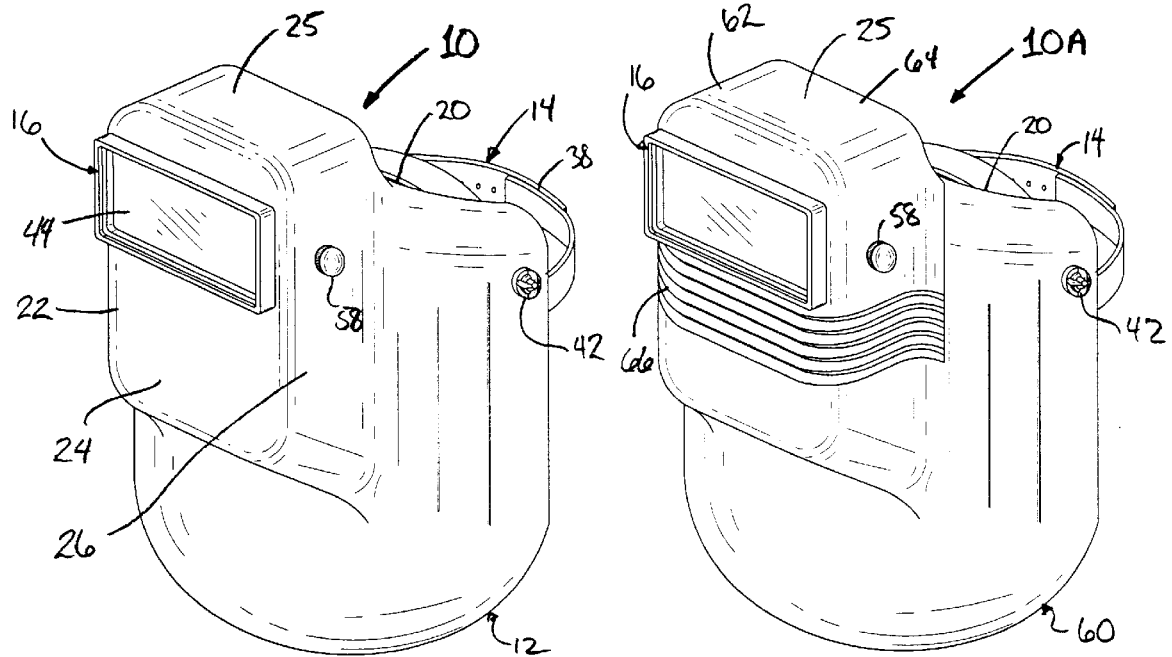
Fig.1.
Fig.2.
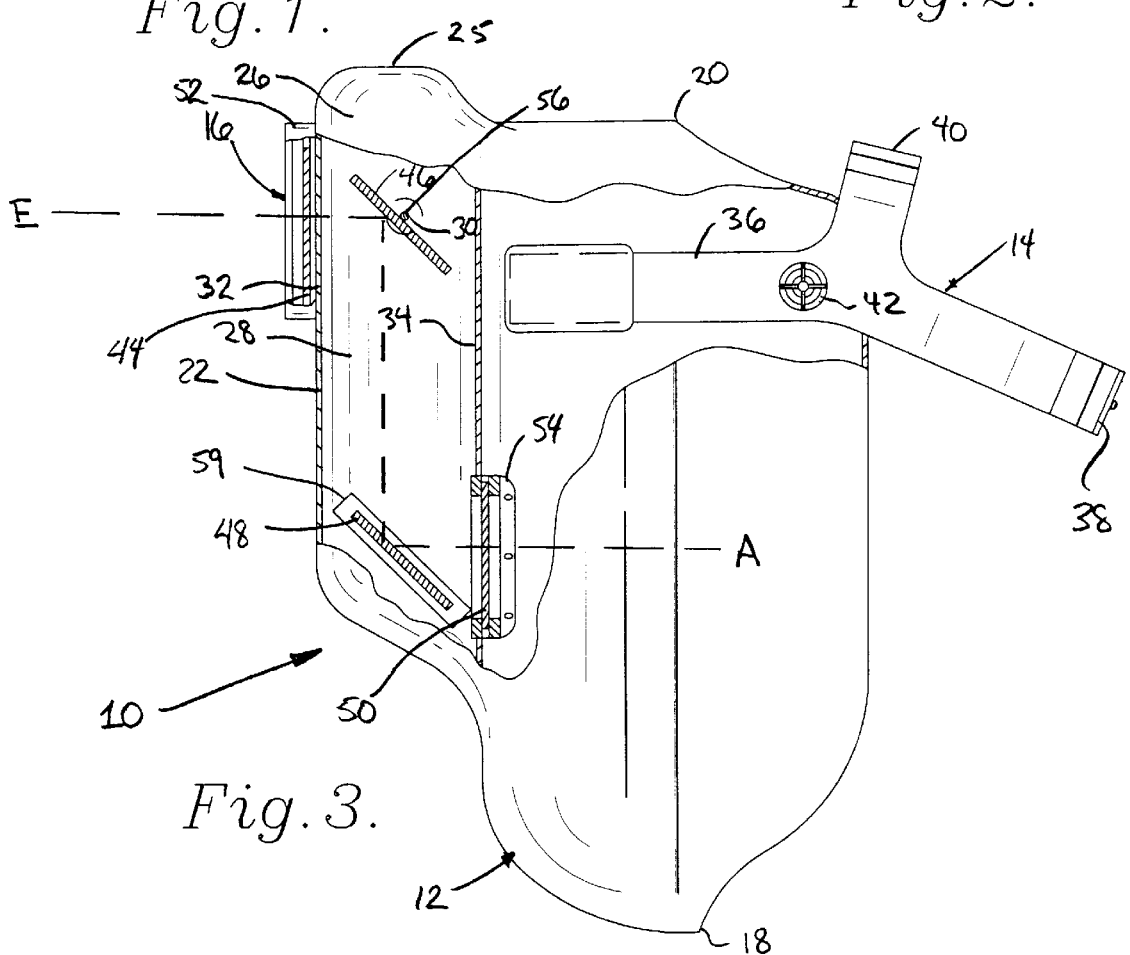
Fig.3.

WELDING HOOD WITH PERISCOPIC VIEW PIECE

BACKGROUND OF THE INVENTION

1. Field of the Invention

The present invention is directed to a welding hood which provides the welder with an extended line of sight capability. More particularly, the invention is concerned with a welding hood having a periscopic view piece, thereby allowing the wearer to view welding activity above the welder's unaided line of sight.

2. Description of the Prior Art

Welding hoods are commonly used to protect the welder's eyes against the brilliance of the welding arc or flame and against sparks and other debris that may be thrown off during the welding operation. Welder's in these circumstances are typically working with hand-held equipment on workpieces within their reach. Such welding hoods typically include a face mask supported by a head band or other mount for supporting the hood on the head of the welder. The face mask includes a view piece which is darkened by colored or filtering glass to shield the wearer's eyes from the brilliant light of the welding arc or flame. Such conventional welding hoods are satisfactory for many welding operations where the welder's head is unobstructed by the working environment and the welder has a direct line of sight through the viewpiece to the workpiece and welding area, but are very limiting in elevated or confined work areas.

Attempts to provide alternatives to the conventional welding hood have resulted in some modest improvements. U.S. Pat. No. 1,885,744 to Malcom shows a welding hood using a tiltable second mirror for directing the image to the wearer's eyes, thereby giving an improved view through the objective window positioned in the direct line of sight of the wearer, but does not extend the wearer's line of sight to view objects above the line of sight and in fact impedes viewing of elevated objects. U.S. Pat. No. 2,211,238 to Links shows a light filter which permits the transmission of harmless light rays and intercepts harmful rays by an arrangement of prisms, but does not enhance the welder's field of vision. U.S. Pat. No. 4,646,363 to Wood shows a welder's helmet which provides two objective lenses to permit direct line-of-sight viewing from the welder's eyes to objects straight ahead and below the hood, but does not enhance the welder's field of vision to a displaced location outside the wearer's direct line of sight. U.S. Pat. No. 5,331,473 to Petersen shows a viewing system used with welding hoods where the objective window is slightly angled downwardly to prevent reflections, but does not enhance the welder's field of vision to enable viewing beyond his ordinary line-of-sight. U.S. Pat. No. 5,398,341 to Trapple provides a hinged objective lens to permit clear, unshielded vision and then a darkened lens where the welder can shift the darkened lens into position without the use of hands, but does not enhance the wearer's line of sight.

There has thus developed a need for an improved welding hood which extends the welder's field of vision above the unaided line of sight and permits viewing over or around obstacles during welding. There has further developed a need for a welding hood which provides a displaced objective window outside and preferably above the welder's usual line of sight, whereby the welder may view the work within reach but blocked from direct viewing by the bulk of the protective mask. There is an additional need for a welding hood which permits the wearer to control the displacement of the objective window relative to his ordinary line of sight to permit optimum viewing of the workpiece within his reach while retaining the convenience and protection of a head-mounted welding hood. Finally, there is a need for an improved welding hood where the wearer may adjust the angle of the view received by a reflecting member so as to provide and enlarged field of view through the displaced objective window.

SUMMARY OF THE INVENTION

These and other objects are largely met by the welding hood with periscopic view piece in accordance with the present invention. The present invention solves the problems discussed above and provides a distinct advance in the state of the art by displacing the welder's view around obstructions. In particular, the welding hood hereof enables a wearer to view welding operations above the wearer's unaided line of sight and extends the incoming field of view by providing a displaced objective window while retaining the convenience of head mounting, protection from harmful light and shielding the welder from dangerous debris.

The present invention broadly includes a welding hood having a face mask, a headband or other mount, and a periscopic view piece. The face mask section carries an image receiving objective window which is displaced and preferably elevated relative to the wearer's unaided line of sight. An opaque housing may be provided on the mask to provide the desired displacement between the line of sight substantially perpendicular to the objective window. The periscopic section includes a first mirror, prism or other reflecting member which is positioned to reflect an image received through the objective window to a second mirror, prism or other reflecting member. The second reflecting member is positioned within the mask to reflect the image to the wearer's eyes and provide proper image orientation to the welder.

In preferred embodiments of the invention, the housing may be provided as an extensible member by a bellows or telescopically received sections, thereby permitting the objective window to be displaced to provide a desired image to aid the welder in his work. Furthermore, the first reflecting member, positioned proximate to the darkened objective window, may be pivotally carried by the mask so as to permit the welder to adjust the angle of view, thereby increasing the range of vision or to provide a desired viewing angle.

These and other advantages provided by the present invention will be readily appreciated by those skilled in the art with reference to the drawings and description of the preferred embodiments of the invention.

BRIEF DESCRIPTION OF THE DRAWINGS

FIG. 1 is a perspective view of the welding hood in accordance with a first embodiment of the present invention, wherein the housing on the hood is fixed and provided with an adjustment knob for tilting a first reflecting member;

FIG. 2 is a perspective view of a second embodiment of the welding hood of the present invention, showing an extensible housing for adjusting the height of the objective window relative to the wearer.

FIG. 3 is a side elevational view thereof, with portions broken away to show the periscopic view piece and the headband for supporting the hood on the head of a welder;

DESCRIPTION OF THE PREFERRED EMBODIMENT

Figure 4:
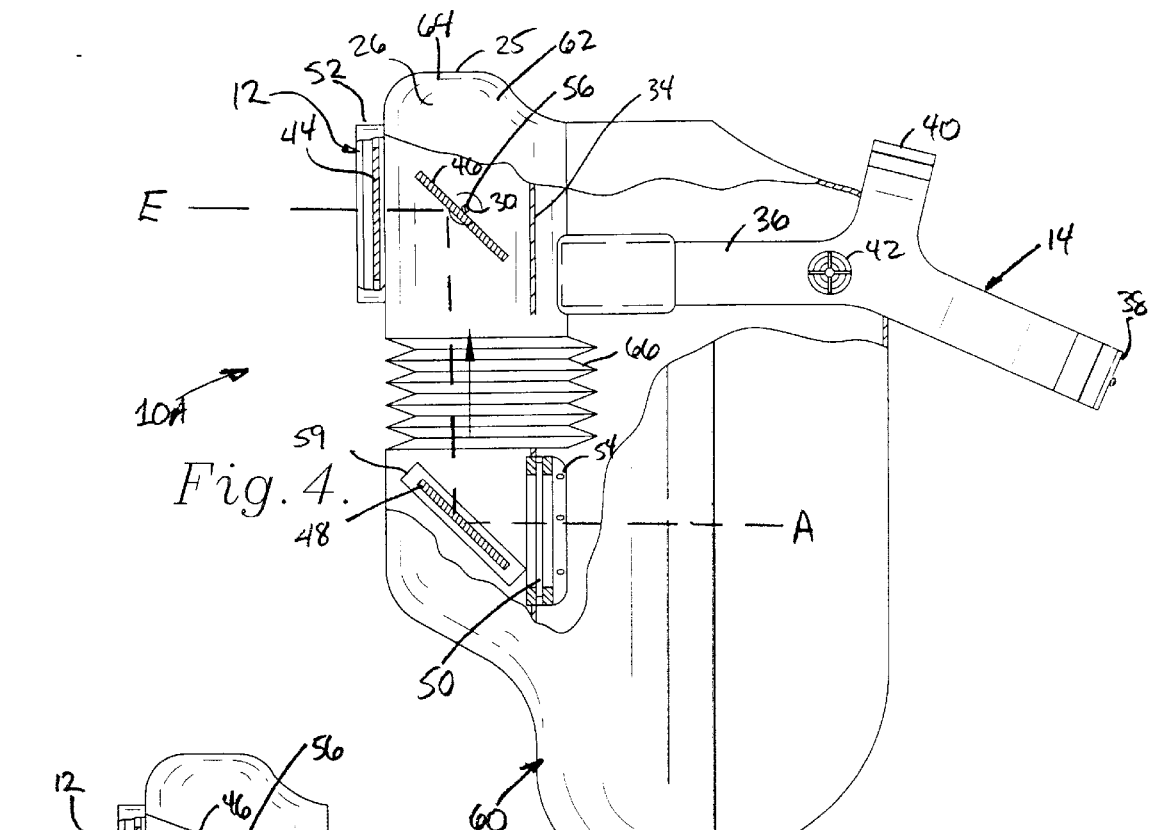
FIG. 4 is a side elevational view thereof, with parts broken away as in FIG. 2, showing the housing being provided with a bellows-type extension in a first, lowered position.

Referring now to the drawings, a first embodiment 10 of the welding hood with periscopic view piece in accordance with the present invention broadly includes a mask 12, a headband 14 for supporting the mask on the head of a welder, and a periscopic view piece 16. The mask 12 may be provided of lightweight steel, aluminum or other metal, or of synthetic resin material suitably resistant to melting or burning as is conventional.

In greater detail, the mask 12 is opaque, and is contoured to wrap around the front of the welder's face. It extends downwardly to a lower margin 18 normally below the welder's neck and upwardly to an upper rim 20. The mask 12 preferably includes a housing 22 which mounts therein the periscopic view piece 16. The housing 22 presents a front wall 24, a roof 25 and a pair of spaced, opposed side walls 26 and 28 which are opaque and effectively shield the view piece 16 from ambient light and debris. The housing 22 projects upwardly from the upper rim 20 and the distance between the side walls 26 and 28 is less than lower portion of the mask which wraps around the welder's face. A hole 30 is provided in each of the side walls 26 and 28. An opening 32 is provided in the front wall 24 to permit an image pass therethrough. A curtain 34, preferably of metal or rigid synthetic resin, depends from the roof 25 to protect the wearer and the view piece 16.

The headband 14 is preferably provided of a plastic material as is conventional and includes sidestraps 36, adjustable backstrap 38 and crown strap 40. A pivot connection 42 is provided to connect each sidestrap 36 with the backstrap 38 and crown strap 40 as is conventional to permit pivoting of the mask 12 upwardly when the welder desires to view the workpiece directly.

The periscopic view piece 16 includes an objective window 44, a first mirror 46 or other reflective member positioned approximately level with the objective window 44 in ordinary use, and a second mirror 48 or other reflective member positioned below the first mirror 46 and level with the position of the welder's eyes as determined by the headband 14. Preferably a viewing window 50 is also provided proximate the welder's eyes. Objective window 44 or viewing window 50 is preferably darkened, such as cobalt glass, to shield the welder's eyes from the harmful rays of the welding arc or flame. Objective window 44 is mounted to the housing 22 of the mask by a mounting bracket 52 in front of the opening 32. Similarly, the viewing window 50 is secured to the mask 12 by a mounting bracket 54. The first mirror 46 is connected to a pivot rod 56 which extends through the holes 30, each end of the rod 56 receiving thereon a knob 58 exterior to the mask 12 for permitting selective tilting of the first mirror 46. The second mirror 48 is preferably fixed relative to the mask 12 at a tilted angle to reflect an image to the welder's eyes from the first mirror 46 and held in position by a mount 59 secured to the side walls 26 and 28.

In use, the welder places the hood 10 on his or her head by positioning the crown strap 40 over the top of the head and the backstrap 38 around the back of the head, adjusting the straps for fit and comfort. The welder's eyes will then be positioned opposite the viewing window 50, but the image is received through the objective window 44. This construction displaces the effective line of sight E above the unaided line of sight A. As used herein, the unaided line of sight A is to be understood as a line extending substantially forwardly toward the mask 12 from the wearer's eyes without the benefit of any reflecting members. By turning one of the knobs 58, the angle of view through the objective window may be adjusted to provide a desired view of the workpiece. The image received through the objective window 44 is darkened by the tinted glass and inverted by the first mirror 46, and then inverted again to return the image to the proper orientation as it is seen by the welder through the view window. The ability to provide an elevated effective line of sight relative to the unaided line of sight is particularly beneficial in welding work such as the exhaust pipes and mufflers of automobiles, where tight working environments may obstruct ordinary hoods and prevent the wearer from seeing the welding operation. The hood 10 hereof is no wider and only slightly lengthier than conventional hoods, and thus provides minimal interference to the user.

Figure 5:
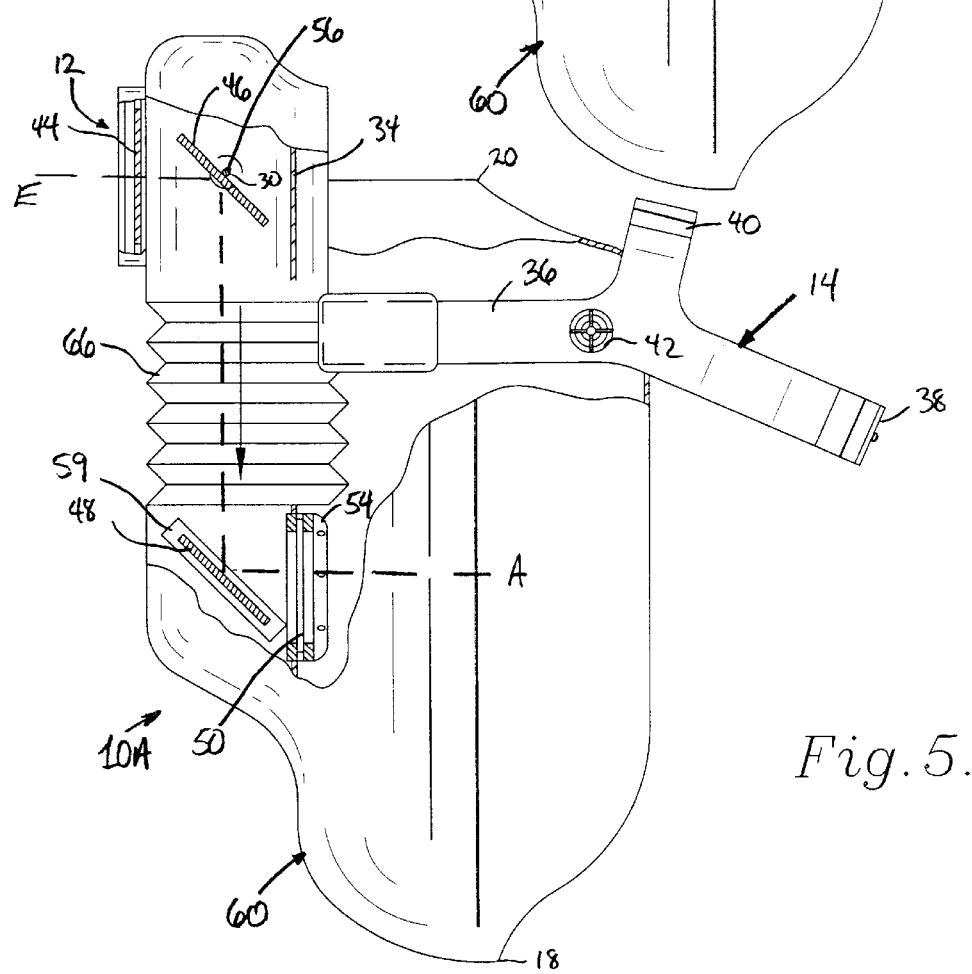
FIG. 5 is a side elevational view similar to FIG. 4, showing the housing in an extended position to elevate the objective window for viewing around obstacles, the first reflecting member being tiltable to provide and improved range of view.

In the alternate embodiment of the welding hood 10A shown in FIGS. 3, 4 and 5, like numbers are used to denote common components. The mask 60 of the welding hood 10A is provided with an extensible housing 62 to provide adjustable displacement between the effective line of sight E and the unaided line of sight A. As shown herein, the housing 62 includes a rigid upper section 64 carrying the objective window 44 and the first mirror 46 and an expansible bellows section 66 interconnecting the upper section 64 and the rigid portion of the mask 60 below the bellows section 66. The bellows section 66 is preferably provided of an opaque self-sustaining synthetic resin which presents corrugated sides 68, or alternatively the bellows section may be provided of a flame-retardant heavy material such as leather or heavy cotton and provided with an innerwire for supporting the upper section 64 at the desired height. Alternative supports could include rods and pivotally mounted clamping collars for holding the upper housing section 64 at a desired displacement. It may be appreciated that telescoping walls or similar structure could be substituted for the bellows. The use of the self-sustaining bellows arrangement as described is preferable, however, as it avoids the necessity of using another hand to manipulate a clamping device to hold the housing 60 at the desired position of adjustment. The upper section 64 is thus not integral with the remainder of the mask 60 as in the welding hood 10 hereof, but rather is shiftable relative to the lower parts of the mask 60 carrying the second mirror 48 and the viewing window 50.

Use of the welding hood 10A is similar to that of the hood 10, but where additional elevation of the effective line of sight E is desired from that shown in FIG. 4, the wearer need not remove his welding gloves but merely grasps the upper housing section 64 and pushes upwardly to thereby elevate the objective window 44 and the first mirror 46. The distance between the sidewalls 26 and 28 is narrower than that of the lower section of the mask 60 as may be seen in FIG. 3, thereby enabling the objective window 44 to extend upwardly into tight spaces otherwise blocking a conventional hood. The welder may then adjust the knobs to tilt the first mirror 46 to change the angle of the effective line of sight E to that most desirable to view the workpiece. The absence of lenses eliminates the need to focus the image when first mirror 46 is shifted relative to the second mirror 48.

Although preferred forms of the invention have been described above, it is to be recognized that such disclosure is by way of illustration only, and should not be utilized in a limiting sense in interpreting the scope of the present invention. Obvious modifications to the exemplary embodiments, as hereinabove set forth, could be readily made by those skilled in the art without departing from the spirit of the present invention. For example, the rod for tilting the first mirror 46 could be provided with mounting brackets and the mounting brackets for the second mirror could be provided integrally with the mask, or adhesive could be substituted for the mounting brackets. Finally, it may be appreciated that the face mask could be provided in the form of a helmet with padding or other suspension members which cushion and position the mask with the reflective members positioned to reflect the image from the elevated effective line of sight to the lower unaided line of sight from the welder's eyes.

The inventor hereby states his intent to rely on the Doctrine of Equivalents to determine and assess the reasonably fair scope of his invention as pertains to any apparatus not materially departing from but outside the literal scope of the invention as set out in the following claims.

What is claimed is:

1. A welding hood comprising:
  a substantially opaque face mask configured to shield the front of a wearer's head during welding, said mask having an opening therein;
  a mounting member connected to said face mask for holding the mask on a welder's head with the opening located above the wearer's unaided line of sight; and
  a view piece mounted on said mask, said view piece including a tinted objective window, a mounting bracket coupling the objective window to the mask adjacent said opening, a first reflective member, a pivot mount pivotally coupling said first reflective member to said mask at an angle to the objective window into the mask along an effective line of sight elevated relative to the unaided line of sight, a second reflective member, and a mount coupling said second reflective member to said mask below the first reflective member and said objective window to receive the reflected image from said first mirror and direct it along the unaided line of sight.

2. The welding hood of claim 1, said pivot mount including a knob accessible from the exterior of the mask.

3. The welding hood of claim 1, wherein said first reflective member is a mirror.

4. The welding hood of claim 1, wherein said second reflective member is a mirror.

5. The welding hood of claim 1, including a viewing window and a bracket coupling the viewing window within the mask and positioning the viewing window along the unaided line of sight.

6. The welding hood of claim 1, said mask including a housing, said objective window and said first reflective member being received in said housing.

7. The welding hood of claim 6, said mask having an upper rim, said housing projecting upwardly from said rim and having first and second side walls presenting a width therebetween less than said mask.

8. The welding hood of claim 6, said mask further including an extensible member for shifting said housing to vary the displacement of said effective line of sight relative to said on aided line of sight.

9. The welding hood of claim 8, wherein said extensible member comprises a self-sustaining bellows.

10. A welding hood comprising:
  a substantially opaque face mask configured to shield the front of a wearer's head during welding, said mask having an opening therein;
  a mounting member connected to said face mask for holding the mask on a welder's head with the opening located above the wearer's unaided line of sight; and
  a view piece mounted on said mask, said view piece including a tinted objective window, a mounting bracket coupling the objective window to the mask adjacent said opening, a first reflective member, a mount coupling said first reflective member to said mask at an angle to the objective window into the mask along an effective line of sight elevated relative to the unaided line of sight, a second reflective member, and a mount coupling said second reflective member to said mask below the first reflective member and said objective window to receive the reflected image from said first reflective member and direct it along the unaided line of sight,
  said mask having an upper rim and including a housing, said objective window and at least said first reflective member being received in said housing, said housing projecting upwardly from said rim and having first and second side walls presenting a width therebetween less than said mask.

11. The mask of claim 10, said mask further including an extensible member for shifting said housing to vary the displacement of said effective line of sight relative to said unaided line of sight.

12. The mask of claim 11, wherein said extensible member comprises a self-sustaining bellows.

13. The mask of claim 11, wherein said mount coupling said first reflective member includes includes a pivotal connection to said mask.

14. A welding hood comprising:
  a substantially opaque face mask configured to shield the front of a wearer's head during welding, said mask having an opening therein;
  a mounting member connected to said face mask for holding the mask on a welder's head with the opening located above the wearer's unaided line of sight; and
  a view piece mounted on said mask, said view piece including a tinted objective window, a mounting bracket coupling the objective window to the mask adjacent said opening, a first reflective member, a mount coupling said first reflective member to said mask at an angle to the objective window into the mask along an effective line of sight elevated relative to the unaided line of sight, a second reflective member, and a mount coupling said second reflective member below the first reflective member and said objective window to receive the reflected image from said first reflective member and direct it along the unaided line of sight,
  said mask including a housing and further including an extensible member for shifting said housing to vary the displacement of said effective line of sight relative to said unaided line of sight.

15. The welding hood of claim 14, wherein said extensible member comprises a self-sustaining bellows.

16. The welding hood of claim 14, wherein said mount coupling said first reflective member includes a pivotal connection to said mask.

17. A welding hood comprising:
  a substantially opaque face mask configured to shield the front of a wearer's head during welding, said mask having an opening therein;
  a mounting member connected to said face mask for holding the mask on a welder's head with the opening located above the wearer's unaided line of sight;

a view piece mounted on said mask, said view piece including a tinted objective window, a mounting bracket coupling the objective window to the mask adjacent said opening, a first reflective member, means mounting said first reflective member at an angle to the objective window into the mask along an effective line of sight elevated relative to the unaided line of sight, a second reflective member, and means mounting said second reflective member below the first reflective member and said objective window to receive the reflected image from said first reflective member and direct it along the unaided line of sight; and a viewing window including a bracket coupling the viewing window within the mask and positioning the viewing window within the mask and positioning the viewing window along the unaided line of sight.

* * * * *